United States Patent [19]

Lange, III et al.

[11] Patent Number: 5,173,408
[45] Date of Patent: Dec. 22, 1992

[54] MAMMALIAN PANCREATIC CHOLESTEROL ESTERASE

[76] Inventors: Louis G. Lange, III, 38 Kingsbury Pl., St. Louis, Mo. 63112; Curtis A. Spilburg, 2230 Willow Ridge La., Chesterfield, Mo. 63017

[21] Appl. No.: 434,899

[22] Filed: Nov. 13, 1989

[51] Int. Cl.$^5$ .................. C12N 15/55; C12N 15/70; C12N 15/85
[52] U.S. Cl. .................. 435/69.1; 435/252.33; 435/252.3; 435/320.1; 435/198; 536/27; 935/9; 935/29; 935/32; 935/73; 935/70
[58] Field of Search .................. 435/69.1–69.9, 435/197, 198, 172.1–172.3, 320.1, 252.3, 252.33; 536/27

[56] References Cited

U.S. PATENT DOCUMENTS 5,017,565  5/1991  Lange, III et al. .................. 514/54
5,063,210  11/1991  Lange, III et al. .................. 514/54

FOREIGN PATENT DOCUMENTS 2274686   1/1976  France .................. 435/71.2
WO89/08456  9/1989  World Int. Prop. O. .................. 514/56

OTHER PUBLICATIONS

Jaye, M., et al., 1983, Nucleic Acids Research, 11(8):2325–2335.
Emtage, J. S., et al., 1983, Proceedings of the National Academy of Sciences, USA, 80:3671–3675.
Windholz, M., et al., Eds., 1983, *The Merck Index*, 10th Ed., Listing No. 4543.
Abonakil, et al., 1988, Biochimica et Biophysica Acta 961:299–308.
Rudd, et al, 1987, Biochimica et Biophysica Acta 918:106–114.
Han, et al., 1987, Biochemistry 26:1617–1625.
Ullrich, et al., 1984, The EMBO Journal 3(2):361–364.
Fitzpatrick, et al., 1988, Journal of Virology 26(11):4239–4248.
Kyger et al., Biochem and Biophys. Res. Commun. 164:1302–1309 (1989).
Vahouny et al., 1964, Proc. J. Exp. Biol. and Med. 116:496.
Bosner et al., 1988, Proc. Natl. Acad. Sci. USA 85:7438.
Allain et al., 1974, Clin. Chem. 20:470.
Calame et al., 1975, Arch. Biochem. Biophys. 168:57.
Labow et al., 1983, Biochem. Byophys. Acta 749:32.
Southern and Berg, 1982, J. Mol. App. Genet. 2:327.

*Primary Examiner*—Robert A. Wax
*Assistant Examiner*—William W. Moore
*Attorney, Agent, or Firm*—Allegretti & Witcoff, Ltd.

[57] ABSTRACT

The invention provides methods for the purification to homogeneity of pancreatic cholesterol esterase in useful quanities from a variety of mammalian species. The gene for a mammalian pancreatic cholesterol esterase has been cloned and sequenced, and is useful for expressing cholesterol esterase in a transformed eukaryotic or prokaryotic cell culture. Thus, methods according to the invention enable the production of large quantities of pancreatic cholesterol esterase for the screening of inhibitors, the production of antibodies, and for commercial purposes related to the alteration of cholesterol/cholesterol ester composition of materials containing free or esterified cholesterol.

3 Claims, 7 Drawing Sheets

FIG. 1

```
         10          20          30          40          50
 *        *  *        *  *        *  *        *  *        *
LGASRLGPSP GCLAVASAAK LGSVYTEGGF VEGVNKKLSL FGDSVDIFKG 60          70          80          90         100
 *        *  *        *  *        *  *        *  *        *
IPFAAAPKAL EKPERHPGWQ GTLKAKSFKK RCLQATLTQD STYGNEDCLY 110         120         130         140         150
 *        *  *        *  *        *  *        *  *        *
LNIWVPQGRK EVSHDLPVMI WIYGGAFLMG ASQGANFLSN YLYDGEEIAT 160         170         180         190         200
 *        *  *        *  *        *  *        *  *        *
RGNVIVVTFN YRVGPLGFLS TGDSNLPGNY GLWDQHMAIA WVKRNIEAFG 210         220         230         240         250
 *        *  *        *  *        *  *        *  *        *
GDPDNITLFG ESAGGASVSL QTLSPYNKGL IKRAISQSCV GLCPWAIQQD 260         270         280         290         300
 *        *  *        *  *        *  *        *  *        *
PLFWAKRIAE KVGCPVDDTS KMAGCLKITD PRALTLAYKL PLGSTEYPKL 310         320         330         340         350
 *        *  *        *  *        *  *        *  *        *
HYLSFVPVID GDFIPDDPVN LYANAADVDY IAGTNDMDGH LFVGMDVPAI 360         370         380         390         400
 *        *  *        *  *        *  *        *  *        *
NSNKQDVTEE DFYKLVSGLT VTKGLRGANA TYEVYTEPWA QDSSQETRKK 410         420         430         440         450
 *        *  *        *  *        *  *        *  *        *
TMVDLETDIL FLIPTKIAVA QHKSHAKSAN TYTYLFSQPS RMPIYPKWMG 460         470         480         490         500
 *        *  *        *  *        *  *        *  *        *
ADHADDLQYV FGKPFATPLG YRAQDRTVSK AMIAYWTNFA RTGDPNTGHS 510         520         530         540         550
 *        *  *        *  *        *  *        *  *        *
YVPANWDPYT LEDDNYLEIN KQMDSNSMKL HLRTNYLQFW TQTYQALPTV 560         570         580         590
 *        *  *        *  *        *  *        *  *
TSAGASLLPP EDNSQASPVP PADNSGAPTE PSAGDSEVAQ MPVVIGF
```

FIG. 2a

```
                              10         20
                     GCCTAGAGGC AGACACTCAC TATGGGGCG
      * 10       * 20       * 30       * 40       * 50
     GCTGGGAGCT AGCCGTCTTG GGCCGTCGCC TGGCTGCTTG GCAGTAGCGA
     30        40          50         60         70
     cCTGGAGGtT CTGTTTCT-T GGC-cTCACC -TGCTGCTTG GCAGcTGCTT
      * 60       * 70       * 80       * 90       * 100
     GTGCAGCGAA GTTGGGCTCC GTATACACCG AAGGCGGCTT CGTGGAGGGC
     80        90          100        110        120
     GTGCTGCAAA GTTGGGTGCT cTGTACACaG AAGGCGGtTT TGTGGAGGGC
      * 110      * 120      * 130      * 140      * 150
     GTCAACAAGA AGCTGAGCCT CTTTGGCGAC TCTGTTGACA TCTTCAAGGG
                                TGG
     130       140         :          160        170
     GTCAACAAGA AACTcAGTCT CTgTGGTGAC TCTGTTGACA TCTTCAAGGG180
      * 160      * 170      * 180      * 190      * 200
     CATCCCCTTC GCTGCCGCCC CCAAGGCCCT GGAGAAGCCC GAGCGACACC
               190         200        210        220
     CATCCCCTTC GCTACC---G CCAAGaCCCT GGAGAATCCT cAGCGTCACC
      * 210      * 220      * 230      * 240      * 250
     CCGGCTGGCA AGGGACCCTG AAGGCCAAGA GCTTTAAGAA ACGGTGCCTG
     230       240         250  A     260        270
     CTGGCTGGCA AGGGACACTG AAGGCtCAG- ACTTcAAGAA ACGATGTCTA
      * 260      * 270      * 280      * 290      * 300
     CAGGCCACGC TCACGCAGGA CAGCACCTAC GGAAATGAAG ACTGCCTCTA
     280       290         300        310        320
     CAAGCCACCa TCACcCAGGA TGATACCTAT GGGcAAGAAG ACTGCCTCTA
      * 310      * 320      * 330      * 340      * 350
     CCTCAACATC TGGGTCCCCC AGGGCAGGAA GGAAGTCTCC CACGACCTGC
     330       340         350        360        370
     TCTCAACATC TGGGTCCCTC AGGGCAGGAA GcAAGTGTCT CATGACCTGC
```

FIG. 2b

```
       *  360         *  370         *  380         *  390         *  400
   CCGTCATGAT    CTGGATCTAT    GGAGGCGCCT    TCCTCATGGG    GGCCAGCCAA
       380           390           400           410           420
   CTGTgATGgT    CTGGATCTAT    GGAGGtGCCT    TCCTCATGGG    GtCTgGCCAg
       *  410         *  420         *  430         *  440         *  450
   GGGGCCAACT    TTCTCAGCAA    CTACCTCTAC    GACGGGGAGG    AGATTGCCAC
       430           440           450           460           470
   GGAGCCAAtT    TTCTCAAgAA    tTACCTgTAt    GAtGGGGAAG    AGATcGCCAC
       *  460         *  470         *  480         *  490         *  500
   ACGGGGCAAC    GTCATCGTGG    TCACGTTCAA    CTACCGCGTT    GGGCCCCTGG
       480           490           500           510           520
   TAGAGcCAAt    GTCATtGTGG    TCACcTTCAA    CTACCGtGTc    GGAcCCtTGG
       *  510         *  520         *  530         *  540         *  550
   GCTTTCTCAG    CACCGGGGAC    TCCAACCTGC    CAGGTAACTA    TGGCCTTTGG
       530           540           550           560           570
   GtTTcCTtAG    CACCGGaGAt    gCTAACCTtC    CAGGTAACTt    TGGACTTcGA
       *  560         *  570         *  580         *  590         *  600
   GATCAGCACA    TGGCCATTGC    TTGGGTGAAG    AGGAACATTG    AGGCCTTCGG
       580           590           600           610           620
   GATCAGCACA    TGGCtATTGC    cTGGGTGAAG    AGGAACATTG    CAGCCTTtGG
       *  610         *  620         *  630         *  640         *  650
   AGGAGACCCC    GACAACATCA    CCCTCTTTGG    GGAGTCGGCC    GGAGGCGCCA
       630           640           650           660           670
   AGGAGACCCC    GAtAACATCA    CCaTCTTTGG    GGAaTCtGCT    GGAGGTGCCA
       *  660         *  670         *  680         *  690         *  700
   GCGTCTCTCT    GCAGACCCTC    TCTCCCTACA    ACAAGGGCCT    CATCAAGCGA
```

FIG. 2c

```
  680        690        700        710        720
TTGTCTCTCT GCAGACCCTC TCCCCATACA ACAAGGGCCT CATCCGGCGA
   * 710     * 720     * 730     * 740     * 750
GCCATCAGCC AGAGTGGAGT GGGTTTGTGC CCTTGGGCCA TCCAGCAGGA
  730        740        750        760        770
GCCATCAGTC AGAGTGGTGT GGCACTGAGC CCCTGGGCCA TCCAGGAGAA
   * 760     * 770     * 780     * 790     * 800
CCCCCTCTTC TGGGCTAAAA GGATTGCAGA GAAGGTGGGC TGCCCCGTGG
  780        790        800        810        820
TCCACTTTTC TGGGCCAAAA CGATCGCTAA GAAGGTGGGA TGCCCCACAG
   * 810     * 820     * 830     * 840     * 850
ACGACACCAG CAAGATGGCT GGGTGTCTGA AGATCACTGA .CCCCCGTGCC
  830        840        850        860        870
.ATGATACCGC CAAGATGGCT GGGTGTCTGA AGATCACAGA TCCCCGAGCC
   * 860     * 870     * 880     * 890     * 900
CTGACGCTGG CCTATAAGCT GCCCCTGGGA AGCACGGAAT ACCCCAAGCT
  880        890        900        910        920
TTGACACTGG CCTACAGGTT GCCCTTGAAA AGCCAGGAGT ACCCCATTGT
   * 910     * 920     * 930     * 940     * 950
GCACTATCTG TCCTTCGTCC CCGTCATCGA TGGAGACTTC ATCCCTGATG
  930        940        950        960        970
GCACTACCTG GCCTTCATCC CTGTCGTCGA TGGTGACTTC ATTCCTGATG
   * 960     * 970     * 980     * 990     * 1000
ACCCCGTCAA CCTGTACGCC AACGCCGCGG ACGTCGACTA CATAGCGGGC
  980        990       1000       1010       1020
ATCCCATCAA CCTGTACGAC AACGCTGCTG ACATTGACTA CTTAGCGGGT
```

FIG. 2d

```
     *   1010      *   1020      *   1030      *   1040      *   1050
    ACCAATGACA  TGGACGGCCA  CCTCTTTGTC  GGGATGGACG  TGCCAGCCAT
    1030        1040        1050        1060        1070
    AttAATGACA  TGGAtGGCCA  CCTgTTTGct  AcAgTTGACG  TGCCcGCCAT

*   1060      *   1070      *   1080      *   1090      *   1100
    CAACAGCAAC  AAACAGGACG  TCACGGAGGA  GGACTTCTAT  AAGCTGGTCA
    1080        1090        1100        1110        1120
    CgACAAGgcC  AAgCAGGAtG  TCACaGAGGA  GGACTTCTAc  AgGCTaGTCA

*   1110      *   1120      *   1130      *   1140      *   1150
    GCGGGCTCAC  CGTCACCAAG  GGGCTCAGAG  GTGCCAATGC  CACGTACGAG
    1130        1140        1150        1160        1170
    GtGGAcAcAC  TGTCgCCAAG  GGGCTtAaAG  GcACCcAAGC  CACcTTTGAc

*   1160      *   1170      *   1180      *   1190      *   1200
    GTGTACACCG  AGCCCTGGGC  CCAGGACTCA  TCCCAGGAGA  CCAGGAAGAA
    1180        1190        1200        1210        1220
    AToTACACTg  AGtCCTGGGC  CCAGGACcCg  TCCCAGGAGA  aCAtGAAGAA

*   1210      *   1220      *   1230      *   1240      *   1250
    GACCATGGTG  GACCTGGAGA  CTGACATCCT  CTTCCTGATC  CCCACAAAGA
    1230        1240        1250        1260        1270
    GACAgTGGTG  GcCTTtGAGA  CTGACATaCT  CTTCCTGATC  CCCACAgAGA

*   1260      *   1270      *   1280      *   1290      *   1300
    TTGCCGTGGC  CCAGCACAAG  AGCCACGCCA  AGAGCGCCAA  CACCTACACC
                            G
    1280        1290        :           1310        1320
    TgGCtcTGGC  CCAGCA-cAG  AcCCATGCCA  AGAGtGCCAA  gACCTACtCt

*   1310      *   1320      *   1330      *   1340      *   1350
    TACCTGTTCT  CCCAACCGTC  TCGGATGCCC  ATCTACCCCA  AGTGGATGGG
```

FIG. 2e

```
     1330       1340       1350       1360       1370
TACCTGTTtT CCCAcCCtTC ACGAATGCCt ATCTACCCaA AaTGGATGGG
   * 1360    * 1370    * 1380    * 1390    * 1400
GGCTGACCAC GCCGATGACC TCCAGTATGT CTTCGGGAAG CCCTTCGCCA
     1380       1390       1400       1410       1420
GGCaGACCAC GCTGATGACC TCCAGTAcGT CTTtGGGAAG CCCTTtGCCA
   * 1410    * 1420    * 1430    * 1440    * 1450
CCCCCCTGGG CTACCGGGCC CAAGACAGGA CTGTCTCCAA GGCCATGATT
     1430       1440       1450       1460       1470
CCCCaCTGGG CTACCGGGCC CAAGACAGGA CTGTCTCCAA GGCCATGATT
   * 1460    * 1470    * 1480    * 1490    * 1500
GCCTACTGGA CCAACTTTGC CAGAACTGGG GACCCTAACA CGGGCCACTC
     1480       1490       1500       1510       1520
GCCTACTGGA CCAACTTTGC CAaGAgTGGG GACCCcAACA TGGGCaACTC
   * 1510    * 1520    * 1530    * 1540    * 1550
GACAGTGCCC GCAAACTGGG ATCCCTACAC CCTGGAAGAT GACAACTACC
     1530       1540       1550       1560       1570
AcCcGTGCCC ACAcACTGGt AcCCtTATAC CATGGAgAAT GGtAACTACC
   * 1560    * 1570    * 1580    * 1590    * 1600
TGGAAATCAA CAAGCAGATG GACAGCAACT CTATGAAGCT GCATCTGAGG
     1580       1590       1600       1610       1620
TGGAcATCAA tAAGaAaATa AcCAGCAcCT CcATGAAGGa GCAcCTAAGG
   * 1610    * 1620    * 1630    * 1640    * 1650
ACCAACTACC TGCAGTTCTG GACCCAGACC TACCAGGCCC TGCCCACGGT
     1630       1640       1650       1660       1670
GAAAAgTtCC TcAAGTTCTG GgCTGTGACa TTCGAGATGC TGCCCACTGT
```

FIG. 2f

```
       .  1660       . 1670       . 1680       . 1690       . 1700
      GACCAGCGCG  GGGGCCAGCC  TGCTGCCCCC  CGAGGACAAC  TCTCAGGCCA
          1680        1690        1700        1710
      ----G-GTTG  GtGaCCAcAC  -T---CCCCC  TGAGGAtGAC  TCAgAGGCTG

.  1710       . 1720       . 1730       . 1740       . 1750
      GCCCCGTGCC  CCCAGCGGAC  AACTCCGGGG  CTCCCACCGA  ACCCTCTGCG
       1720        1730        1740        1750        1760
      cCCCCGTcCC  ACCTACAGAC  gACTCCcAGG  GTGGTCCTGT  cCCAcCTACA

.  1760       . 1770       . 1780       . 1790       . 1800
      GGTGACTCTG  AGGTGGCTCA  GATGCCTGTC  GTCATTGGTT  TCTAATGTCC
       1770        1780        1790        1800        1810
      GATGACTCTc  AGacAAcACc  GGTGC-cccC  AACAgACAAC  TCTc-AGgCT .  1810       . 1820       . 1830       . 1840       . 1850
      TTGGCCTCCA  GGGGCCACAG  GAGACCCCAG  GGCCCACTTC  CCTCCCAAGT
       1820        1830        1840        1850        1860
      GGTGAC-TCT  GTGGAgg-CT  cAGATGCCTG  GTCCCATTGG  CTTCTAAAG- .  1860       . 1870       .
      GCCTCCTGAA  TAAAGCCTCA  ACCATCTC(PoLy A)
        1870
      TCC-TATAAA  ccGGGgC
```

5,173,408

MAMMALIAN PANCREATIC CHOLESTEROL ESTERASE

BACKGROUND OF THE INVENTION

1. Field of the Invention

The invention relates to enzymes involved in the metabolism of cholesterol and more specifically to the cholesterol esterase secreted by the pancreas in mammals. Cholesterol metabolism is of critical interest to those involved in protecting human health. Atherosclerosis is the leading cause of death in the United States and reduction of serum cholesterol levels has recently been embraced as a national health priority. See NIH Consensus Panel Report, J.A.M.A. 253: 2094 (1985). NIH recommendations include measurement of serum cholesterol in all adults, with efforts to reduce cholesterol in those individuals with levels above 200 mg %. In this regard front line therapy is a reduction in the amount of cholesterol and triglycerides ingested, followed by the use of agents that interfere with absorption of ingested lipids. See Consensus Full Report, Arch. Inst. Med. 148: 36 (1988).

Pancreatic cholesterol esterase plays a pivotal role in the absorption of cholesterol and fatty acids. The inhibition of cholesterol esterase could lead to reduced serum cholesterol levels. Numerous approaches to developing inhibitors of cholesterol esterase will likely be attempted, including the use of chemical inhibitors. Therapeutic biologicals, such as monoclonal or polyclonal antibodies to pancreatic cholesterol esterase have great potential. In particular, antibodies against purified cholesterol esterase can be isolated from the milk of immunized cows and used as an ingestible therapeutic. Analogs of pancreatic cholesterol esterase are proteins similar to cholesterol esterase, but with sufficient variation in amino acid sequence to bind cholesterol esters without releasing free cholesterol and fatty acids. If such analogs can be developed they will serve as powerful inhibitors of cholesterol esterase function.

Whatever type of inhibitor is being developed, large quantities of highly purified enzyme are required to test the efficacy of any potential inhibitor, as well as to better understand the enzyme and thus allow the development of further therapeutic means. There is, therefore, a need for methods to purify useful quantities of homogeneous pancreatic cholesterol esterase. In addition, for the preparation of analog inhibitors, the amino acid sequence of the enzyme and its underlying DNA sequence must be known. Thus, there is a need for a cloned DNA sequence encoding cholesterol esterase, from which the DNA and amino acid sequences may be determined.

Finally, pancreatic cholesterol esterase has considerable commercial utility for enzymatic hydrolysis or synthesis of ester linkages in the preparation of biologicals or foodstuffs such as dairy products. There is, therefore, a need for a means of producing commercially significant, large-scale quantities of homogeneous cholesterol esterase, especially from cows, which cannot be met by purification of the enzyme from natural sources. What is needed, then, is a means for producing pancreatic cholesterol esterase through the use of recombinant DNA expression vectors in a suitable host cell or organism, as well as a means of large-scale purification of the enzyme so expressed.

2. Information Disclosure

Borja et al., 1964, Proc. J. Exp. Biol. and Med. 116: 496, teach that cholesterol esterase is secreted by the pancreas, and that its catalysis of cholesterol ester hydrolysis to produce free cholesterol and free fatty acids is essential for the absorption of cholesterol. Bosner et al., 1988, Proc. Natl. Acad. Sci. USA 85: 7438, teach that cholesterol esterase performs its function while anchored to the intestinal membrane via a receptor-like interaction with brush border membrane associated heparin. Lange and Spilburg, in co-pending application U.S. Ser. No. 340,868, teach sulfated polysaccharide inhibitors of human pancreatic cholesterol esterase which are effective in blocking the absorption of cholesterol and fatty acids into intestinal cells.

Numerous procedures for the preparation of pancreatic cholesterol esterase have been reported See, e.g., Allain et al., 1974, Clin. Chem. 20: 470, Calame et al., 1975, Arch. Biochem. Byophys. 168: 57, Labow et al., 1983, Biochem. Byophys. Acta 749: 32. In general, the reported procedures are tedious and give poor yields of heterogeneous material. Production of significant quantities of homogeneous material has not been achieved. For example, the commercially available cholesterol esterase, prepared by the method of Allain et al., is less than 5% pure according to both physical and functional assays. None of the existing preparative procedures has been useful for purifying cholesterol esterase from several different mammalian species.

BRIEF SUMMARY OF THE INVENTION

The present invention is directed toward the preparation of useful quantities of homogeneous mammalian pancreatic cholesterol esterase. The invention encompasses methods for large-scale purification of pancreatic cholesterol esterase from natural sources or from prokaryotic or eukaryotic cell cultures producing recombinant mammalian pancreatic cholesterol esterase. The invention also comprises mammalian pancreatic cholesterol esterases purified according to such methods, and the use of such purified enzymes to produce and purify antibodies to such enzymes, and to screen potential inhibitors to such enzymes. In addition, the invention comprises the use of such purified enzyme to alter the cholesterol composition of food-stuffs and biologics.

The invention further comprises cloned DNA sequences encoding mammalian pancreatic cholesterol esterase, expression vectors containing such DNA sequences, and prokaryotic or eukaryotic cell cultures harboring said expression vectors, whereby said cell cultures are capable of producing mammalian pancreatic cholesterol esterase. The invention additionally comprises a process for commercial-scale production and purification of mammalian pancreatic cholesterol esterase through the application of the aforementioned purification methods to the supernatants of said mammalian pancreatic cholesterol esterase-producing cell cultures. The invention finally comprises homogeneous mammalian pancreatic cholesterol esterase produced by such a process.

BRIEF DESCRIPTION OF THE DRAWINGS

FIG. 1 shows the amino acid sequence for bovine pancreatic cholesterol esterase, as deduced from the nucleotide sequence shown in FIG. 2.

FIG. 2 shows the nucleotide sequence of the cDNA encoding bovine pancreatic cholesterol esterase.

DETAILED DESCRIPTION OF THE INVENTION

Large-scale purification to homogeneity of mammalian pancreatic cholesterol esterase from human, bovine, porcine, and rat pancreas has now been achieved through the use of sulfated matrices in affinity chromatography. This is the first method ever to allow purification of this enzyme from all mammalian species tested. The major form of the enzyme purified from bovine pancreas has a molecular weight of 72 kilodaltons (kDa) and has never before been detected.

The observation that certain sulfated polysaccharides can decrease cholesterol absorption was recently disclosed in co-pending application U.S. Ser. No. 340,868, which is incorporated herein by reference. The sulfated polysaccharides reported in that investigation have the characteristic of binding to mammalian pancreatic cholesterol esterase. Thus, it is possible to use these compounds as an affinity matrix for the purification of pancreatic cholesterol esterase. Pancreatic cholesterol esterase contains a specific sulfate recognition site which allows it to bind to a large number of sulfated compounds which include, but are not limited to, heparin-agarose, Mono S, SP-Sephadex, cellulose sulfate, pectin sulfate, chitin sulfate, chitosan sulfate and 2, 3, or 6-congeners of chitosan sulfate, agar sulfate, amylopectin sulfate and any combination of monomers or polymers of the above. Those skilled in the art will recognize that other polysaccharides or resins may become sulfated through the action of chlorosulfate, sulfur dioxide, or other sulfating agents, whereby, in view of the above, such sulfated polysaccharides or resins could be employed as affinity matrices for the purification of pancreatic cholesterol esterase. Preferably, sulfated polysaccharides are used as the affinity matrix. In particular, sulfated cellulose which has been sulfated to an extent insufficient to make it soluble in water or heparin agarose are most preferred.

The binding of sulfated polysaccharides by pancreatic cholesterol esterase involves one or more specific regions of the protein, one of which in the rat protein is represented by the amino acid sequence MDGHLFATVDVPAIDKAKQDV. Those skilled in the art will recognize that the sulfate binding sites of the human, porcine, and bovine pancreatic cholesterol esterase enzymes, and of mammalian pancreatic cholesterol esterase enzymes will have substantially the same amino acid sequence. Substantially the same amino acid sequence is understood to mean an amino acid sequence in which any amino acid substitutions are conservative and do not significantly affect the function of the protein or any domain or region thereof (e.g., the ability of the region described above to bind to sulfated polysaccharides).

Purification of the enzyme takes advantage of the affinity of the enzyme, principally through its sulfate binding site, for a sulfated matrix. A solution comprising the pancreatic cholesterol esterase is applied to the sulfated matrix. The solution must be provided at a salt concentration and pH sufficient to allow the pancreatic cholesterol esterase to bind to the sulfated matrix. A variety of low salt concentrations will allow binding. Most preferably, binding is allowed to occur in 25 mM acetate, 50mM benzamidine at a pH of 5 1. The use of a buffer at this pH and the presence of benzamidine serve to inhibit proteolysis. Prior art procedures have failed to address the problem of proteolysis during purification. This is believed to be the reason that the major form (72 kDa) of the bovine enzyme has never been detected previously, even though it may be related structurally as a derivative of the previously described 67 kDa bovine enzyme.

After binding of the pancreatic cholesterol esterase to the sulfated matrix has occurred, contaminating proteins can be removed by washing the column with a solution at a salt concentration and pH sufficient to allow continued binding of the pancreatic cholesterol esterase to the sulfated matrix. This may be achieved through the use of either a single wash solution or a linear salt gradient. For example, sulfated resins are preferably washed with linear salt gradients, whereas sulfated polysaccharides, including cellulose-sulfate and heparin-agarose are most preferably washed with a single wash solution at a higher salt concentration because these matrices bind the enzyme with higher affinity. Pancreatic cholesterol esterase is finally eluted from the sulfated matrix by washing the matrix with a solution at a salt concentration and pH sufficient to inhibit the binding of the enzyme to the sulfated matrix. When a linear salt gradient is employed, fractions are collected and the enzyme will be present in fractions at higher salt concentrations. Alternatively, when sulfated polysaccharides are utilized as the affinity matrix, the enzyme can be collected with a single wash utilizing a solution of a sulfated bile salt, such as taurocholate. Preferred sulfated matrices with conditions for binding and elution are described in Example 5. Combinations of matrices can be used for purification to homogeneity and other preliminary steps may be included. The bovine major (72 kDa) species, for example, was purified by the sequential chromatography steps of S-Sepharose with a linear salt gradient, SP-Sephadex with a linear salt gradient and mono-S with a linear salt gradient. Human pancreatic cholesterol esterase, in contrast, was preliminarily fractionated over hydroxylapatite and AcA-34, followed by purification on heparin-sepharose with a single high salt elution step.

The ability to purify to homogeneity significant quantities of mammalian pancreatic cholesterol esterases in general and human pancreatic cholesterol esterase in particular, allows for the first time on a large scale the production of antibodies to human pancreatic cholesterol esterase, as well as to other mammalian pancreatic cholesterol esterases. The homogeneous enzyme is used to immunize cows which produce antibodies to the enzyme and secrete it into their milk. The antibodies are readily purified from the milk by affinity chromatography using a binding component comprising homogeneous pancreatic cholesterol esterase cross-linked to an inert matrix. In this manner large quantities of purified antibodies highly specific for pancreatic cholesterol esterase are readily prepared. Such antibodies, particularly antibodies to human pancreatic cholesterol esterase, can be used as inhibitors to pancreatic cholesterol esterase and might lead to reduced serum cholesterol levels.

FIG. 1 shows the amino acid sequence deduced from the nucleotide sequence shown in FIG. 2 of bovine pancreatic cholesterol esterase. The amino acid sequence in FIG. 1 further enables the production of antibodies to peptides comprising less than a complete pancreatic cholesterol esterase molecule. Such peptides may be prepared by chemical synthesis or by proteolytic or chemical cleavage of the purified enzyme. The peptides may be used alone to immunize cows or may be coupled to a carrier protein, such as keyhole limpet hemocyanin (KLH). In either case the antibodies would be purified from cow's milk using affinity chromatography with the purified enzyme as the binding component, as described above.

The present invention provides, for the first time, useful quantities of homogeneous pancreatic cholesterol esterase. Thus the homogeneous enzyme composition can be used to screen potential inhibitors of pancreatic cholesterol esterase for their ability to modify enzyme properties, such as release of free cholesterol from fatty acyl cholesterol esters, or binding of immobilized heparin.

The ability to produce useful quantities of this enzyme in pure form further allows for the use of the enzyme in commercial applications. In particular, the purified enzyme will be used to alter the cholesterol/cholesterol ester composition of foodstuffs and biologics through its catalytic function. The bile salt taurocholate is required at concentrations above 1 mM for esterase activity whereas in the absence of taurocholate or in the presence of low concentrations of taurocholate (i.e., less than 250 μM) the enzyme will operate to esterify cholesterol. Thus, both increases and decreases in free cholesterol in biologics or foodstuffs may be moderated by the same enzyme by simply altering the conditions.

The present invention provides also, for the first time, a composition of homogeneous mammalian pancreatic cholesterol esterase, especially the bovine 72 kDa species, in sufficient quantity for amino acid sequence analysis. Those skilled in the art will recognize that the ability to carry out such an analysis greatly enhances the probability of successfully cloning the gene encoding the underlying peptide sequence. Amino acid sequence determination allows the determination of a finite set of nucleotide sequences which can encode a particular peptide, based upon the genetic code. Within such a finite set of nucleotide sequences will be found a smaller set of nucleotide sequences which are more likely to encode the particular peptide, on the basis of the codon usage preference of the organism from which the gene is to be isolated.

Once a tissue source which expresses the protein of interest has been identified, mRNA can be isolated from this source. The mRNA can be used to synthesize cDNA, from which a library can be prepared. A mixture of oligonucleotides corresponding to the subset of nucleotide sequences most likely to encode a peptide from the protein can then be used to screen the library for the presence of a cDNA encoding the protein of interest.

In the case of mammalian pancreatic cholesterol esterase, the pancreas has long been known in the art as the tissue source expressing this enzyme. We have additionally discovered that expression of this enzyme in the pancreas of adult cows greatly exceeds that of calf pancreas. Thus, mRNA was prepared from adult bovine pancreas by standard procedures, and used for the synthesis of cDNA, according to procedures well known in the art. A cDNA library was prepared by conventional methods.

Conventional N-terminal amino acid sequence analysis of the homogeneous composition of bovine pancreatic cholesterol esterase, prepared as described herein, allowed the synthesis of a mixed oligonucleotide probe of the following sequence:

```
A
5'- GCCTTCCACAAAGCCGCCTTCGGTATACAC-3'
    T  C      G     C    G
    C
```

This probe mixture was shown to hybridize very strongly in Northern blots of mRNA isolated from adult bovine pancreas to an mRNA species of 1.9 kb. No detectable hybridization was observed when mRNA isolated from calf pancreas was used. The probe was then used to identify a hybridizing clone from the cDNA library. The clone was isolated and a plasmid containing a full-length cDNA encoding pancreatic cholesterol esterase was excised therefrom. The nucleotide sequence of the cDNA was determined according to procedures well known in the art. The amino acid sequence for the entire bovine protein is shown in FIG. 1, as deduced from the nucleotide sequence shown in FIG. 2. The predicted peptide sequence is 578 amino acids in length and has a molecular weight of 63.5 kDa in the absence of glycosylation. There are two potential N-glycosylation sites. The theoretical isoelectric point of the unglycosylated protein is 5.1.

Thus, the present invention encompasses a cloned DNA sequence encoding mammalian pancreatic cholesterol esterase. For purposes of defining this aspect of the invention, a cloned DNA sequence will be interpreted to mean a DNA molecule comprising two portions: a (1) specific nucleotide sequence, covalently attached to (2) another DNA molecule portion which is capable of autonomous replication within a bacterial, yeast, plant, insect or mammalian cell, wherein the autonomously replicating DNA molecule is not a bacterial, yeast, plant, insect or mammalian chromosome, and whereby the cloned DNA sequence and attached autonomously replicating DNA molecule are capable of replicating autonomously as a unit within a bacterial, yeast, plant, insect or mammalian cell. Thus, a cloned DNA sequence may refer to a cloning vector that contains a specific nucleotide sequence encoding a cholesterol esterase. A DNA sequence encoding mammalian pancreatic cholesterol esterase is defined as a DNA sequence which, when transcribed and translated in a cell will give rise to a protein which is capable of releasing oleic acid from cholesteryl oleate, and is also capable of liberating palmitic acid from palmitoyl lysophosphatidyl choline. A representative DNA sequence encoding a mammalian pancreatic cholesterol esterase is the bovine sequence shown in FIG. 2. Those skilled in the art will recognize that the disclosure relating the cloning of this DNA sequence coupled with the DNA sequence shown in FIG. 2 fully enables the cloning of other mammalian pancreatic cholesterol esterases including those from humans, pigs, and rats. DNA sequences encoding any mammalian pancreatic cholesterol esterase, as defined above are enabled and contemplated by the present invention.

A recombinant expression vector encoding a mammalian pancreatic cholesterol esterase can readily be prepared by methods well known in the art. Such a vector comprises the DNA sequence encoding a mammalian pancreatic cholesterol esterase, a promoter of other DNA sequence recognized by RNA polymerase as a signal for the initiation of transcription, and an origin of replication which allows the vector to replicate in a bacterial, yeast, plant, insect, or mammalian cell.

Cell culture expression systems have been extensively discussed in the art. Most preferred are mammalian cell culture expression systems, particularly the systems involving CHO(dhfr-) cells. In such a system, a recombinant expression vector encoding and capable of expressing the pancreatic cholesterol esterase can be introduced into CHO(dhfr-) cells together with a plasmid encoding and capable of expressing dhfr. Transfected cells can be selected in selective media, for example, hypoxanthine-glycine-thymidine (HGT) media. Subsequent amplification of transfected DNA can be mediated by growing transfected cells in media containing methotrexate. Expression may be assayed by activity assays carried out using culture supernantants or through well established immunological procedures.

The following examples are shown by way of illustration and not by way of limitation.

EXAMPLE 1

Purification of Human Pancreatic Cholesterol Esterase

Human pancreas was received at autopsy. About 30 g of tissue in 10 mM phosphate, pH 6.0, 50 mM benzamidine, 0.5% digitonin were homogenized with a polytron, centrifugally pelleted (48,000× g, 30 min.) and the supernatant collected. The supernatant was centrifugally pelleted (100,000× g, 60 min.) again and the second supernatant was passed through glass wool and dialized overnight against 50 mM benzamidine, 10 mM phosphate, pH 6.8. The dialysate was loaded onto a hydroxylapatite column (2.6×10 cm) equilibrated with 50 mM benzamidine, 10 mM phosphate, pH 6.8. The column was washed with identical buffer, then developed with a linear gradient of 50 mM to 350 mM phosphate. pH 6.8, 50 mM benzamidine. The cholesterol esterase activity eluted at a conductivity of 20-22 mS/cm. These fractions were pooled and loaded onto an AcA34 column (Bio-Rad Laboratories, Inc., 2200 Wright Avenue, Richmond, Calif. 94804) (2.6×90 cm) equilibrated with 500 mM NaCl, 10 mM phosphate, pH 6.0. The fraction emerging at an apparent molecular weight of 350 kDa contained cholesterol esterase activity and was dialyzed against 10 mM phosphate, pH 6.0.

The enzyme was applied to heparin Sepharose (Pharmacia Inc., 800 Centennial Avenue, Piscataway, N.J. 08854) equilibrated with the same buffer. The resin was then washed with five to 10 column volumes of 50 mM NaCl, 50 mM benzamidine, 10 mM Tris, pH 7.2 followed by two column volumes of 20 mM taurocholate, 30 mM NaCl, 50 mM benzamidine, 10 mM Tris, pH 7.2. Purified enzyme is then eluted in 500 mM NaCl, 10 mM Tris, pH 7.2, 50 mM benzamidine.

EXAMPLE 2

Purification of Bovine Pancreatic Cholesterol Esterase

Commercially available bovine pancreatic cholesterol esterase (Sigma Chemical Co., P.O. Box 14509, St. Louis, Mo. 63178; purity<1%) in 10 mM Tris, pH 7.2, was applied to heparin-Sepharose (Pharmacia Inc., 800 Centennial Avenue, Piscataway, N.J. 08854) (1.5×10 cm) equilibrated with the same buffer. The resin was developed further by washing with 0.10M NaCl, 10 mM Tris, pH 7.2 Little or no activity was found in any of these preliminary steps, even though virtually all of the applied protein was eluted. When the absorbance at 280 nm returned to zero, the resin was washed with 20 mM sodium taurocholate containing sodium chloride to give a conductivity of 13 to 15 mS/cm, the same conductivity as that of the previous washing buffer. All the activity was eluted in several fractions. This single purification step typically provided a 60 to 80% yield with a 50- to 100-fold purification and gives a single band at 67 kDa on SDS-PAGE. No additional activity was found when the resin was washed with higher concentrations of salt and the resin could be regenerated by washing with 2.0M NaCl, 10 mM Tris, pH 7.2. The large purification factor achieved by this single step indicates that heparin is acting as an affinity ligand for cholesterol esterase, a property demonstrated further by using different elution conditions. Thus, when the charged resin was washed with heparin (2 mg/ml), greater than 95% of the enzyme was eluted from the resin, while chondroitin sulfate (5 mg/ml), another sulfated mucopolysaccharide, removed less than 2% of bound enzyme.

EXAMPLE 3

Purification of Porcine Pancreatic Cholesterol Esterase

The same procedure described in Example 2 for the human enzyme was used for porcine pancreatic cholesterol esterase. In this case, active enzyme was found at 15 to 17 mS/cm from the hydroxylapatite column, and emerged from the AcA 34 gel filtration column (Bio-Rad Laboratories, 2200 Wright Avenue, Richmond, Calif. 94804) at a molecular weight of 81 kDa. This procedure provides homogeneous enzyme with molecular weight 81 kDa in 25% yield.

EXAMPLE 4

Purification of Bovine 72 kDa Major Species Pancreatic Cholesterol Esterase

Supernatant from bovine pancreas homogenate was prepared according to Example 1 as described for the human enzyme. The supernatant was chromatographed over S-Sepharose (Pharmacia Inc., 800 Centennial Avenue, Piscataway, N.J. 08854) in 25 mM acetate pH 5.1, 50 mM benzamidine. The enzyme was eluted from the column using a linear salt gradient from 175 mM NaCl to 500 mM NaCl. The eluate was loaded onto a SP-Sephadex (Pharmacia Inc., 800 Centennial Avenue, Piscataway, N.J. 08854) column in 25 mM acetate, pH 5.1, 50 mM benzanidine, then eluted with a linear gradient of 0 mM to 120 mM NaCl. The eluate contained two bands exhibiting cholesterol esterase activity, one at 72 kDa (90-99%) and one at 67 kDa (1.10%). The 72 kDa form was completely separated from the 67 kDa form by chromatography over a mono-S column (Pharmacia Inc., 800 Centennial Avenue, Piscataway, N.J. 08854).

EXAMPLE 5

Purification of Cholesterol Esterases Using Sulfated Cellulose Columns

A. Preparation of Sulfated Cellulose Columns

Cellulose was lightly sulfated to maintain its insolubility and this material was used as a potent matrix for isolating and purifying the enzyme. Thus, 2.5 g of cellulose (type 100) was suspended in 50 ml water and 12.5 g of sulfur trioxide pyridine complex were added with stirring. After one hour at room temperature, 100 ml of dimethylformamide were added, and the mixture was stirred for an additional 30 minutes. The cellulose sulfate was collected by centrifugation. After washing six times with water, the resin was packed in a small column (0.9×9 cm).

B. Purification of Cholesterol Esterases

Resins such as those described in part A of this example and the other sulfated polysaccharides can be used to purify cholesterol esterases. For example, bovine cholesterol esterase was pumped onto the resin in 25 mM acetate, pH 5.1 at 15 ml/hr. All the activity was bound. but in this case, binding was so strong that even 2M NaCl in 25 mM acetate, pH 5.1 did not remove the enzyme. Elution with 100 mM taurocholate, a sulfated bile salt, removed all the activity in virtually 100% yield. Heparin agarose also functions as an effective affinity matrix for cholesterol esterase in the same manner.

EXAMPLE 6

Assays for Cholesterol Esterase Activity

Cholesterol esterase activity was determined by measuring the release of $[^{14}C]$-oleic acid from vesicles containing cholesteryl 1-$[^{14}C]$-oleate. Vesicles were prepared by drying under nitrogen a solution of 1.00 ml of 1.33 mM egg phosphatidylcholine in hexane and 1.27 ml of 1 mM cholesteryl oleate containing 10 $\mu$l of cholesteryl 1-$[^{14}C]$-oleate ($2.2 \times 10^6$ cpm) in chloroform. The precipitate was resuspended in 10 ml of 0.15M Tris, pH 7.5, vortexed vigorously for several seconds and then sonicated on ice for 20 minutes under nitrogen. Following sonication, the preparation was centrifuged at $48,000 \times$ g for 60 minutes, and the vesicle preparation was carefully decanted and stored at 4° C. In a typical assay, 75 $\mu$l of cholesteryl $[^{14}C]$-oleate vesicles, 25 $\mu$l of 100 mM taurocholate, 175 $\mu$l of 0.15M Tris, pH 7.5 were mixed in a test tube and hydrolysis was initiated by adding 25 $\mu$l of enzyme to the reaction mixture at 37° C. After a known time, usually five minutes, the reaction was quenched by addition of 600 $\mu$l of 0.3N NaOH and 3 ml of benzene:methanol:chloroform (1:1.2:0.5). After mixing. the samples were centrifuged and 1 ml of the clear organic phase was removed and counted for radioactivity. Since only part of the sample was removed for counting, an efficiency sample was prepared by adding 100 $\mu$l of $[^{14}C]$-oleic acid vesicles of known specific radioactivity to 200 $\mu$l of 0.15M Tris, pH 7.5. The same manipulations were performed on this sample as those described above for assay. The efficiency of transfer was then determined by dividing the number of counts in the 1 ml organic phase by the dpm in 100 $\mu$l of starting $[^{14}C]$-oleic acid vesicles. Activity is expressed as nanomoles of oleic acid released/ml/hour and was less than 0.1 nmol/ml/hr in the absence of added enzyme. To assess the potential inhibition of chemical compounds, these agents are added to the incubation mixture before addition of cholesterol esterase and the ratio of $[^{14}C]$-oleate release determined as above and compared to the ratio observed in the absence of the test compound.

EXAMPLE 7

Preparation of Rabbit IgG Fraction Against 67 kDa Bovine Pancreatic Cholesterol Esterase Five hundred micrograms of homogeneous 67 kDa protein were emulsified in Freund's complete adjuvant (CFA) and injected subcutaneously into a New Zealand White rabbit. Twenty-one days later the rabbit was boosted with intraperitoneal injections of 250 $\mu$g protein dissolved in 1 ml of 10 mM sodium phosphate, 150 mM NaCl, pH 7.1. The rabbits were bled 10 days later and the presence of anti-cholesterol esterase IgG was determined on Ouchterlony plates. Rabbit IgG was purified by passing 20 ml of rabbit serum over a protein A Sepharose (Pharmacia, Inc., 800 Centennial Avenue, Piscataway, N.J. 08854) column equilibrated with 20 mM Tris, 20 mM NaCl, pH 8.0. The resin was washed with equilibration buffer followed by 20 mM Tris, 0.5% deoxycholate, 500 mM NaCl, pH 8.0 and then equilibration buffer. Finally, the IgG was eluted with 100 mM glycine pH 2.8. Similarly, 2 mg of homnogeneous human cholesterol esterase emulsified in CFA are injected into four subcutaneous sites in a cow, and booster injections of 1 mg protein at three and six weeks are made. Secretory antibodies are elicited in the cow's milk that are directed at human cholesterol esterase and can be separated from other milk proteins by ammonium sulfate precipitation and ion-exchange chromatography.

EXAMPLE 8

Construction and Screening of Bovine Pancreas cDNA Library

A. Construction of Bovine Pancreas cDNA Library

Total RNA was extracted from bovine pancreas with 5.5M guanidine thiocyanate, as described by Han et al., 1987, Biochemistry 26:1617-1625; poly A+ RNA was purified from total RNA by chromatography on oligo dT-cellulose (Pharmacia Inc., 800 Centennial Avenue, Piscataway, N.J. 08854). A cDNA library was constructed using 5 $\mu$g of twice-selected poly A+ RNA using a Pharmacia cDNA synthesis kit according to the method of Gubler and Hoffman, 1983, Gene 25: 263-269. The EcoRI-ended double-stranded cDNA was ligated into EcoRI-digested and dephosphorylated λ-ZAP vector arms (Stratagene, 11099 North Torrey Pines Road, La Jolla, Calif. 92037), and packaged using a Stratagene kit. About 300,000 to 500,000 independent, recombinant clones were obtained.

B. Preparation of Probe for Screening the cDNA Library

Total RNA and poly A+ RNA were isolated from pancreas of adult cow or calf as described in part A of this example. RNA was denatured with formaldehyde and formamide and electrophoresed on a 1% agarose-formaldehyde gel containing 2.2M formaldehyde. RNA was transferred by capillary action to a nylon membrane (Schleicher and Schuell, Inc , 10 Optical Avenue, Keene, N.H. 03431) in 20× SSPE. A 30-mer probe mixture was synthesized based upon N-terminal amino acid sequence determined from purified bovine pancreatic cholesterol esterase. The probe mixture:

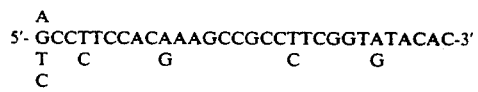

was labelled using $\alpha$-$[^{32}P]$-ATP and polynucleotide kinase. The probe mixture hybridized strongly to a single 1.9 kb band in lanes containing total RNA or poly A+ RNA from adult bovine pancreas, but did not hybridize to lanes containing total RNA or poly A+ RNA from calf pancreas.

C. Screening Bovine Pancreas cDNA Library

The radiolabelled probe described in part B of this example was used to probe the cDNA library constructed as described in part A of this example. The library was screened by plaque hybridization in the presence of 0.25% nonfat dry milk in 6× SSPE. Prehybridization and hybridization were conducted at 60° C.

A bluescript plasmid was excised from the hybridizing λ-Zap clones by co-infecting XLI-Blue cells with positive λ-Zap phage and R-408 helper phage. Excision from the plasmid of a cDNA clone encoding the entire cholesterol esterase protein was performed, with identification in the cDNA sequence of both the N-terminal protein sequence and the sequence of the 30-mer probe given in part B of this example. Bluescript plasmids were harvested by the alkaline lysis method of Birnboin, 1983, Meth. Enzymol 100: 243-255.

EXAMPLE 9

DNA Sequence Analysis of cDNA for Cholesterol Esterase

Each sequencing reaction used approximately 3 μg of double-stranded pBluescript plasmid with positive inserts and 50 ng of sequencing primer. Double-stranded plasmid was denatured for 5 minutes at room temperature with 0.2M NaOH, 0.2 mM ethylene diamine tetraacetate (EDTA) (final concentrations); DNA was precipitated with 0.18M ammonium acetate, pH 5.4 (final concentration) and 2.5 volumes of ethanol. The mixture was chilled on dry ice for 15 minutes and the DNA pellet was spun down for 10 minutes in a microfuge. The pellets were washed with 70% ethanol and vacuum dried. The inserts were sequenced by the dideoxy chain termination method of Sanger et. al., 1977, Proc. Natl. Acad. Sci. USA 74: 5463-5467 using Sequenase TM 2.0 (U.S. Biochemical Corporation, P. O. Box 22400, Cleveland, Ohio 44122) or AMV reverse transcriptase sequencing kit (Stratagene, 11099 North Torrey Pines Road, La Jolla, Calif. 92037). Internal sequences for both strands were obtained by sequential nested primers, 18 to 20 nucleotides in length. The DNA sequence thus obtained is shown in FIG. 2.

EXAMPLE 10

Construction of Expression Vectors

The eukaryotic-prokaryotic shuttle vector pSV2neo has been described by Southern and Berg, (1982) J. Mol. App. Genet. 2: 327-341. A vector capable of expressing bovine pancreatic cholesterol esterase in mammalian cells is prepared by inserting the full-length cDNA (FIG. 2) isolated as described in Example 8, into pSV2neo in such a way as to replace the neo gene, and thus be flanked by the SV-40 early promoter upstream and the SV-40 polyadenylation signal downstream. The insert in the cDNA clone is first site-directed mutagenized to remove a single EcoRI restriction site within the cDNA and then the insert is removed by digesting the cDNA clone with EcoRI. The 1.9 kb insert is isolated by electroelution. The EcoRI ends are converted to blunt ends by incubation of the DNA fragment in the presence of Klenow polymerase and 10 μm dNTPS for 5 minutes. The neo gene is removed from pSV2neo by digestion with HindIII and SmaI and the 4.4 kb vector fragment is isolated by electroelution. The HindIII end is converted to a blunt end using Klenow polymerase. The isolated and blunt-ended fragments are then ligated together by the use of T4 DNA ligase and T4RNA ligase (10:1 unit ratio) in the presence of 100 μm ATP and 50 mM MgCl$_2$ at room temperature for about three hours. A portion of the ligation mixture is used to transform competent HB101 E. coli bacteria, which are selected for ampicillin resistance. The orientation of the insert is determined by DNA sequencing, as described in Example 9.

EXAMPLE 11

Expression of Bovine Pancreatic Cholesterol Esterase in CHO cells

The expression vector described in Example 10 is co-introduced into DHFR deficient CHO cells along with a plasmid expressing the DHFR gene, by the method of Graham and Van der Eb, 1973, J. Virology 52: 456-467. The plasmid expressing DHFR is prepared as described in Example 10, except that the DHFR gene from the plasmid pE342.HBV.E400.D22 is used in place of the bovine pancreatic cholesterol esterase gene. The plasmid pE342.HBV.E400.D22 is described in U.S. Pat. No. 4,853,330. Transfected cells are selected in HGT medium. Resistant colonies are tested for expression of pancreatic cholesterol esterase by collecting their media supernatants and utilizing them in the assay described in Example 6. Clones found to be expressing cholesterol esterase are seeded at 200,000 cells per 100 nM plate in 50 mM methotrexate (MTX) to select for DNA amplification. Cells surviving the initial MTX selection are tested again for cholesterol esterase activity. Those cells showing an increase in cholesterol esterase activity, relative to pre-amplification activity levels, are then further selected for amplification in 500 nM MTX. Resistant cells showing additional increases in cholesterol esterase activity are finally selected for optimum amplification in 10,000 nM MTX. Those subclones resistant to 10,000 nM MTX which produce the highest levels of cholesterol esterase activity are used as producer cell lines to provide cholesterol esterase which, after purification as described in Example 4, can be used to screen for enzyme inhibitors, produce anti-enzyme antibodies or alter the cholesterol/cholesterol ester composition of foodstuffs.

EXAMPLE 12

Synthesis of Cholesterol Esters by Cholesterol Esterase

Bovine pancreatic cholesterol esterase was incubated at pH 6.0 with 900 μm $^{14}$C-oleate and 700 μm cholesterol or with cholesteryl-[$^{14}$C]-oleate, at varying concentrations of the bile salt taurocholate. Ester synthesis in the former case was assayed by determining the rate of formation of cholesteryl-[$^{14}$C]-oleate and in the latter case as described in Example 6. The synthesis and hydrolytic rates and the ratios between them at various concentrations of taurocholate are shown below in Table I. Rates are expressed as μmoles of product formed per mg of enzyme per hour.

TABLE I

| | Taurocholate, mM | | | |
| --- | --- | --- | --- | --- |
| | 0 | 0.1 | 1.0 | 10.0 |
| Synthetic | 0.83 | 14.2 | 32.5 | 78.3 |
| Hydrolytic | 0 | 0 | 12.0 | 73.5 |
| Ratio+ | — | — | 2.7 | 1.1 |

These results indicate that the enzyme can be made to act primarily as a synthetic enzyme at appropriate concentrations of taurocholate below 1 mM. Thus, the enzyme can be used to alter the cholesterol/cholesterol ester composition of a given solution by simply adding enzyme and adjusting the level of taurocholate from 0 to 1 mM. Above 1 mM taurocholate, the enzyme is useful for the general hydrolysis of cholesterol esters. Thus, free cholesterol in foodstuffs such as liquid dairy products can be converted into esterified cholesterol, which may be more poorly absorbed than free cholesterol or whose absorption may be inhibited through the oral ingestion of sulfated polysaccharides (see, for example, U.S. Ser. Nos. 340,868, 425,109 and co-pending U.S. application entitled, "The Use of Sulfated Polysaccharides To Decrease Cholesterol and Fatty Acid Absorption", filed Oct. 31, 1989, all of which are hereby incorporated by reference).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A process for producing homogeneous mammalian pancreatic cholesterol esterase, the process comprising the following steps:
   (a) growing, in appropriate media an *E. coli* cell culture transformed with an expression vector encoding mammalian pancreatic cholesterol esterase, where the transformed *E. coli* cell culture is capable of expressing mammalian pancreatic cholesterol esterase;
   (b) collecting the *E. coli* cells;
   (c) lysing the *E. coli* cell to form a cell lysate;
   (d) loading the cell lysate onto a sulfated matrix, wherein the concentrations of salt and the pH of the cell lysate is sufficient to allow the cholesterol esterase to bind the sulfated matrix and benzamidine is included in the solution to inhibit proteolysis;
   (e) removing non-binding protein immpurities by washing the matrix with a solution comprising a concentration of salt and pH sufficient to allow continued binding of the cholesterol esterase to the matrix; and
   (f) eluting the cholesterol esterase from the matrix with a solution comprising a concentration of salt and pH sufficient to inhibit binding of the cholesterol esterase to the matrix.

2. A process for producing homogeneous mammalian pancreatic cholesterol esterase, the process comprising the following steps:
   (a) growing, in appropriate media, a mammalian cell culture transformed with an expression vector encoding a mammalian pancreatic cholesterol esterase, wherein the transformed mammalian cell culture is capable of expressing and secreting a mammalian pancreatic cholesterol esterase;
   (b) collecting the media supernatant;
   (c) loading the media supernatant onto a sulfated matrix, wherein the concentration of salt and the pH of the media supernatant is sufficient to allow the cholesterol esterase to bind the sulfated matrix and benzamidine is included in the solution to inhibit proteolysis;
   (d) removing non-binding protein impurities by washing the matrix with a solution comprising a concentration of salt and pH sufficient to allow continued binding of the cholesterol esterase to the matrix; and
   (e) eluting the cholesterol esterase from the matrix by washing the matrix with a solution comprising a concentration of salt and pH sufficient to inhibit binding of the cholesterol esterase to the matrix.

3. The method according to claim 2, wherein the mammalian pancreatic cholesterol esterase is human pancreatic cholesterol esterase.

* * * * *